United States Patent
Buono

(10) Patent No.: US 7,014,991 B2
(45) Date of Patent: Mar. 21, 2006

(54) USE OF INJECTABLE DYES FOR STAINING AN ANTERIOR LENS CAPSULE AND VITREO-RETINAL INTERFACE

(75) Inventor: Lawrence M Buono, Philadelphia, PA (US)

(73) Assignee: Infinite Vision, LLC, Exton, PA (US)

( * ) Notice: Subject to any disclaimer, the term of this patent is extended or adjusted under 35 U.S.C. 154(b) by 429 days.

(21) Appl. No.: 10/170,287

(22) Filed: Jun. 13, 2002

(65) Prior Publication Data

US 2003/0096334 A1 May 22, 2003

Related U.S. Application Data

(63) Continuation-in-part of application No. 10/073,737, filed on Feb. 11, 2002.
(60) Provisional application No. 60/361,801, filed on Mar. 5, 2002, and provisional application No. 60/334,470, filed on Nov. 16, 2001.

(51) Int. Cl.
  *C12N 5/00* (2006.01)

(52) U.S. Cl. .................. 435/1.1; 435/40.5; 435/325; 128/890

(58) Field of Classification Search .............. 435/1.1, 435/40.5, 325; 128/898
See application file for complete search history.

(56) References Cited

U.S. PATENT DOCUMENTS

| 5,167,618 | A | | 12/1992 | Kershner |
| 5,196,449 | A | * | 3/1993 | Magistretti et al. |
| 6,013,640 | A | * | 1/2000 | Elliott et al. |
| 6,299,603 | B1 | | 10/2001 | Hecker et al. |
| 6,367,480 | B1 | * | 4/2002 | Coroneo |
| 2002/0173464 | A1 | * | 11/2002 | King et al. |
| 2003/0000913 | A1 | | 1/2003 | Schwartz et al. |
| 2003/0097117 | A1 | * | 5/2003 | Buono et al. |

FOREIGN PATENT DOCUMENTS

WO    WO 97/36622 A1    10/1997

* cited by examiner

*Primary Examiner*—Leon B. Lankford, Jr.
(74) *Attorney, Agent, or Firm*—Caesar, Rivise, Bernstein, Cohen & Pokotilow, Ltd.

(57) ABSTRACT

A method of staining an ocular structure, the structure being a human or other mammalian eye or portion thereof, the method comprising staining the ocular structure with either indigotindisulfonate, Patent Blue V, Sulphan Blue, tolonium chloride, or Evans Blue. Ocular structures of particular interest are the anterior lens capsule and the vitreo-retinal interface.

10 Claims, No Drawings

USE OF INJECTABLE DYES FOR STAINING AN ANTERIOR LENS CAPSULE AND VITREO-RETINAL INTERFACE

CROSS REFERENCE TO RELATED APPLICATIONS

This application claims the benefit of U.S. provisional application Ser. No. 60/334,470, which was filed Nov. 16, 2001 and is incorporated by reference herein in its entirety. This application is also a continuation-in-part of application Ser. No. 10/073,737, which was filed Feb. 11, 2002, and is incorporated by reference herein in its entirety. This application claims the benefit of U.S. provisional application Ser. No. 60/361,801, which was filed Mar. 5, 2002 and is incorporated by reference herein in its enirety.

BACKGROUND OF THE INVENTION

The present invention relates to lens capsule staining as part of the process of cataract surgery. It is common in modern cataract surgery to remove a portion of the anterior lens capsule while preserving the majority of the capsular bag structure in order to facilitate artificial lens implantation. This surgical method at times may be difficult to accomplish because of a variety reasons, including difficulty in properly visualizing the lens capsule. The present invention is intended to decrease that difficulty by staining the anterior lens capsule, thereby aiding in its visualization for safe removal.

The present invention is also related to the staining of the vitreo-retinal surface. A pathological process can occur at the vitreo-retinal interface that can alter the natural architecture. Using modern vitreo-retinal surgical techniques, an attempt is made to separate this interface and restore the normal anatomical architecture. This surgical technique at times may be difficult to accomplish because of a variety of reasons, including difficulty in properly visualizing various tissues. The present invention is intended to decrease that difficulty by staining the vitreo-retinal surface, thereby aiding in its visualization for safe removal.

BRIEF SUMMARY OF THE INVENTION

In a general aspect, the process of the invention is a method of staining an ocular structure, said structure being a mammalian eye (especially a human eye) or portion thereof, said method comprising staining said structure with a dye selected from the group consisting of indigotindisulfonate, Patent Blue V, Sulphan Blue, tolonium chloride, or Evans Blue, said staining done by direct application of said dye.

In particular exemplary embodiments, the dye includes one of the following: Indigo Carmine (indigotindisulfonate), Patent Blue V, Sulphan Blue, tolonium chloride, or Evans Blue. Athough it is preferred to use a single dye when staining a given structure, the invention contemplates staining with a combination of two or more of the five dyes.

In particular embodiments of the invention, the staining is performed during intra-ocular surgery, especially cataract surgery or vitreo-retinal surgery. Intra-ocular structures of particular interest are the lens capsule, especially the anterior lens capsule, and the internal limiting membrane of the retina.

DETAILED DESCRIPTION OF THE INVENTION

The dyes are preferably administered in a non-solid form. Preferred formulations of the dye are solutions, suspensions, and gels. An example of preferred solution formulation is an aqueous solution buffered to a physiologically acceptable pH. The amount of dye administered to the ocular structure is enough to stain the structure. Nevertheless excess amounts of the dye are avoided so as to minimize or eliminate undesired staining of structures, especially those other than the anterior lens capsule.

Commercial formulations of the dyes are available from many companies (e.g., Akorn, May & Baker, ICI Pharmaceuticals, and American Regent Laboratories). The dye concentration is preferably about 0.1% to 6.5%, depending on the type of dye and the amount ofinjection. The dye concentration can also vary from less than 0.1% to over 6.5%, as desired for the particular use. The dye is preferably administered so as to stain the anterior lens capsule while sparing other intra-ocular structures, especially the posterior surface of the cornea, as much as possible. The dyes are also described in greater detail below as used for staining.

Indigotindisulfonate's alternative names, formulations, designations, and applicable information include, but are not limited to the following: indigo carmine; Blue X, ceruleinum; Cl Food Blue 1; Colour Index No. 73015; Disodium Indigotin-5,5'-disulphonate; E132; FD & C Blue No. 2; Indigocarminium; Indigotindisulfonate Sodium (USAN); Indigotine; Sodium Indigotindisulphonate; Disodium 3,3'-dioxo-2,2'-bi-indolinylidene-5,5'-disulphonate. $C_{16}H_8N_2Na_2O_8S_2$=466.4. CAS-860-22-0.

Indigotindisulfonate is, for example, available from American Reagent Laboratories, Inc., Shirley N.Y., which has a formulation of the dye under the trade name of Indigo Carmine Injection (Indigotindisulfonate sodium, USP). It is supplied as a 5 ml sterile ampule containing 40 mg of indigotindisulfonate sodium in water for intravenous injection and pH when necessary with citric acid and/or sodium citrate.

Patent Blue V (e.g., Acid Blue 3; CI Food Blue 5; Colour Index No. 42051; E131. Calcium α-(4-diethylaminophenyl)-α-(4-diethyliminiocyclohexa-2,5-dienylidene)-5-hydroxytoluene-2,4-disulphonate $(C_{27}H_{31}N_2O_7S_2)_2Ca$=1159.4) is a dark blue-violet powder. Aqueous solutions are blue in color. Preferred injections of Patent Blue V are 2.5%, in ampoules of 2 mL.

Sulphan Blue (e.g., (BAN) Acid Blue 1; Alphazurine 2G; Blue VRS; Colour Index No. 42045; Isosulfan Blue (USAN); Patent Blue V; Sulphanum Caeruleum. Sodium α-(4-diethylaminophenyl)-α-(4-diethyliminiocyclo-hexa-2,5-dienylidene)toluene-2,5-disulphonate. $C_{27}H_{31}N_2NaO_6S_2$=566.7) is a violet powder. Solutions are blue in color. Traditionally, injections of Sulphan Blue are 6.2% in ampoules of 10 mL.

Tolonium chloride (e.g., Toluidine Blue O, 3-Amino-7-(Dimethylamino)-2-Methylphenothiazin-5-ium Chloride; CI Basic Blue 17), is a dark green powder and is slightly soluble in water. Tolonium chloride must be used carefully so as to avoid injury to the cornea and conjunctiva.

Evans Blue (e.g Azovan Blue (BAN) Azovanum Caeruleum; CI Direct Blue 53; Colour Index No.23860; Evans Blue (USAN); T-1824. Tetrasodium 6.6'-[3,3'-dimethylbiphenyl-4,4'-diylbis(azo)]bis[4-amino-t-hydroxynaphthalene-1,3-disulphonate]. $C_{34}H_{24}N_6Na_4O_{14}S_4$=960.8) is a green, bluish-green, or brown, odorless powder. It is very soluble in water. The U.S.P. injection has a pH of 5.5 to 7.5. Preferably it is stored in airtight containers.

A novel reason to use the dyes is during cataract surgery: surgery in which the natural lens is removed while leaving the lens capsule in its natural anatomic location and in which an artificial lens is inserted in its place. The purpose of the dyes is to make the anterior lens capsule more easily visible to the surgeon.

An example of cataract surgery is as follows: A small paracentesis incision is made peripherally into the clear cornea. The aqueous humor of the anterior chamber is subsequently drained and replaced with air. The indigotindisulfonate dye is then applied to the anterior lens surface (anterior lens capsule) using an appropriate delivery device (e.g., a spray device comprising a fluid reservoir, a cannula with a distal tip for insertion into the eye and with an orifice located inwards of the distal tip, and a pressurizer arranged to move fluid from the reservoir through the orifice to an intraocular structure) such as that disclosed in application Ser. No. 10/073,737, which was filed Feb. 11, 2002. The dye is allowed to contact the lens surface for an amount of time sufficient to stain that surface. Optionally, the dye solution is drained or irrigated (using balanced salt solution) from the anterior chamber. Next the anterior chamber is filled with an optically clear viscoelastic polymer (e.g., hyaluronate, chondroitin sulfate). A rent is made in the anterior lens capsule using a cystosome and a continuous curvilinear capsulorrhexis is then made under direct visualization of the stained anterior lens capsule.

Such a procedure can be done as has been done for a number of years with other dyes to stain the anterior lens capsule. The dyes that have been described previously are fluorescein, indocyanine green, and methylene blue.

Although not important for carrying out the present invention, it is theorized here that the staining occurs at the lens capsule basement membrane.

An advantage of using one of the listed dyes (e.g., Indigo Carmine, Patent Blue V, Sulphan Blue, tolonium chloride, Evans Blue), compared to using currently used dyes such as indocyanine green, is that the listed dyes are relatively inexpensive. Another advantage is that the lens capsule stained with any of those dyes is more easily visualized than lens capsule stained with either indocyanine green or fluorescein.

Another reason to use the listed dyes is during vitreo-retinal surgery to restore the natural architecture of the vitreo-retinal surface. The purpose of the dye is to make the distinction between the interface of the vitreous and the retina more easily visible.

A method of vitreo-retinal surgery is as follows: A standard three-port vitrectomy is employed. After a partial or complete vitrectomy is performed, the vitreous compartment is filled with gas. The dye is then applied to the surface of the vitreo-retinal interface using an appropriate delivery device as described above. The dye is allowed to contact the vitreo-retinal interface for an amount of time sufficient to stain that interface. Next, the desired tissue (e.g., posterior hyaloid membrane and/or internal limiting membrane), now more easily visible, is removed using appropriate forceps.

What is claimed is:

1. A method of staining an ocular structure, said structure being a mammalian eye or portion thereof, said method comprising staining said structure with indigotindisulfonate, said staining done by direct application of said indigotindisulfonate.

2. The method of claim 1 wherein the mammalian eye is a human eye.

3. The method of claim 2 wherein the staining is performed during intra-ocular surgery.

4. The method of claim 3 wherein the intra-ocular surgery is cataract surgery.

5. The method of claim 3 wherein the intra-ocular surgery is vitreo-retinal surgery.

6. The method of claim 2 wherein the ocular structure is an intra-ocular structure.

7. The method of claim 6 wherein the intra-ocular structure is a lens capsule.

8. The method of claim 7 wherein the lens capsule is an anterior lens capsule.

9. The method of claim 6 wherein the intra-ocular structure is the internal limiting membrane of the retina.

10. The method of claim 6 wherein the intra-ocular structure is the vitreous.

* * * * *